US012502487B2

(12) United States Patent
Zhang et al.

(10) Patent No.: US 12,502,487 B2
(45) Date of Patent: Dec. 23, 2025

(54) INJECTION PEN NEEDLE

(71) Applicant: Zhejiang Kindly Medical Devices Co., Ltd., Zhejiang (CN)

(72) Inventors: Qian Zhang, Zhejiang (CN); Yong Zhang, Zhejiang (CN); Jianguang Wang, Zhejiang (CN); Hong Chen, Zhejiang (CN); Xu Chen, Zhejiang (CN); Zhuoyuan Lou, Zhejiang (CN); Yuanlong Zheng, Zhejiang (CN)

(73) Assignee: Zhejiang Kindly Medical Devices Co., Ltd., Wenzhou (CN)

( * ) Notice: Subject to any disclaimer, the term of this patent is extended or adjusted under 35 U.S.C. 154(b) by 833 days.

(21) Appl. No.: 17/732,209

(22) Filed: Apr. 28, 2022

(65) Prior Publication Data

US 2022/0347392 A1 Nov. 3, 2022

(30) Foreign Application Priority Data

Apr. 29, 2021 (CN) ......................... 202120911108.1

(51) Int. Cl.
*A61M 5/32* (2006.01)
*A61M 5/315* (2006.01)
*A61M 5/20* (2006.01)

(52) U.S. Cl.
CPC ...... *A61M 5/3272* (2013.01); *A61M 5/31571* (2013.01); *A61M 5/3243* (2013.01); *A61M 5/3271* (2013.01); *A61M 2005/208* (2013.01); *A61M 5/3202* (2013.01); *A61M 2005/3247* (2013.01); *A61M 2005/3254* (2013.01); *A61M 5/326* (2013.01); *A61M 2005/3267* (2013.01)

(58) Field of Classification Search
CPC .............. A61M 5/3272; A61M 5/3271; A61M 2005/3267; A61M 2005/3247; A61M 5/326; A61M 5/3202; A61M 5/3243; A61M 2005/3254
See application file for complete search history.

(56) References Cited

U.S. PATENT DOCUMENTS

2015/0051578 A1* 2/2015 Herr .................. A61M 5/31553 604/110

FOREIGN PATENT DOCUMENTS

CN 1788805 A * 6/2006
CN 107823761 A 3/2018
(Continued)

OTHER PUBLICATIONS

CN 1788805, English language machine translation (Year: 2006).*
WO 2014109012, English Language machine translation (Year: 2014).*

*Primary Examiner* — Wesley G Harris

(57) ABSTRACT

The present disclosure provides an injection pen needle, which includes a needle head, a needle seat, an outer sleeve, a sliding sleeve and a limit ring, wherein the needle head is arranged on the needle seat; the needle seat comprises baffle plates; the outer sleeve is arranged on the needle seat in a sleeving manner; the lower part of the sliding sleeve enters the outer sleeve and is adapted to move up and down in the outer sleeve, and a channel hole, from which the needle head can penetrate out, is formed in the top of the sliding sleeve; the limit ring is arranged in the outer sleeve; the limit ring comprises sliding blocks; the bottom of the sliding sleeve pushes against the limit ring; and when the sliding sleeve moves up and down in the outer sleeve.

9 Claims, 5 Drawing Sheets

(56) References Cited

FOREIGN PATENT DOCUMENTS

| | | | | |
|---|---|---|---|---|
| CN | 110141733 | A | * | 8/2019 |
| CN | 111529822 | A | | 8/2020 |
| CN | 211512959 | U | | 9/2020 |
| WO | WO-03011378 | A1 | * | 2/2003 |
| WO | WO-2006111864 | A1 | * | 10/2006 |
| WO | WO-2014109012 | A1 | * | 7/2014 |
| WO | WO-2014112426 | A1 | * | 7/2014 |
| WO | WO-2014115241 | A1 | * | 7/2014 |
| WO | 2020019154 | A1 | | 1/2020 |
| WO | 2020119832 | A2 | | 6/2020 |

* cited by examiner

INJECTION PEN NEEDLE

CROSS-REFERENCE TO RELATED APPLICATION

This application claims priority from the Chinese patent application 202120911108.1 filed Apr. 29, 2021, the content of which is incorporated herein in the entirety by reference.

TECHNICAL FIELD

The present disclosure relates to the technical field of medical instruments, and particularly relates to an injection pen needle.

BACKGROUND ART

An injection pen needle, which is usually used as a disposable injection tool, is used cooperatively with a pen-injector, and for example, the injection pen needle is used cooperatively with an insulin pen-injector for injecting insulin. The existing injection pen needle comprises a needle seat, a needle head and a sliding sleeve; the needle head is arranged in the needle seat; when in use, the needle head is connected with an injector; the sliding sleeve is pressed to enable the needle head to stretch out of the needle seat to inject drugs into a body of a patient; after injection is completed, the sliding sleeve rebounds to an original position; the needle head is covered by the sliding sleeve again, so as to avoid puncturing; however, when in follow-up discarding, a processing person is very easy to press the sliding sleeve in a processing process, so that the needle head is exposed again and is very easy to puncture hands, and therefore, a greater potential safety hazard exists.

SUMMARY OF THE UTILITY MODEL

The problem solved by the present disclosure is how to avoid puncturing as a needle head stretches out again after use when a sliding sleeve is pressed again.

In order to solve the above problem, the present disclosure provides an injection pen needle, which comprises: a needle head, a needle seat, an outer sleeve, a sliding sleeve and a limit ring, wherein the needle head is arranged on the needle seat; the needle seat comprises baffle plates; the outer sleeve is arranged on the needle seat in a sleeving manner; the lower part of the sliding sleeve enters the outer sleeve and is adapted to move up and down in the outer sleeve, and a channel hole, from which the needle head can penetrate out, is formed in the top of the sliding sleeve; the limit ring is arranged in the outer sleeve; the limit ring comprises sliding blocks; the bottom of the sliding sleeve pushes against the limit ring; and when the sliding sleeve moves up and down in the outer sleeve, the limit ring is adapted to rotate relatively to the sliding sleeve to enable the sliding blocks to move to the positions which are above the baffle plates.

With respect to the prior art, the injection pen needle of the present disclosure has the following beneficial effects: the sliding blocks on the limit ring push against the sliding sleeve and is slidingly connected with the sliding sleeve, so that when the sliding sleeve moves downwards, the needle head stretches out of the sliding sleeve, so as to carry out injection; meanwhile, due to downward movement of the sliding sleeve, the sliding sleeve pushes the limit ring to move; after injection is completed, when pressure on the sliding sleeve is removed, the sliding sleeve moves upwards to shield the needle head in the sliding sleeve again, and meanwhile, the sliding blocks on the limit ring are rotated to the positions which are above the baffle plates; and when the sliding sleeve is pressed again due to false touch and the like, the sliding blocks lean against the baffle plates to limit the sliding sleeve to move downwards further, so as to effectively avoid that the needle head is exposed again.

Optionally, sliding bevels are formed at the bottom of the sliding sleeve, the sliding bevels push against the sliding blocks, and the sliding blocks are adapted to move along the sliding bevels. Therefore, a locking ring is rotated through movement of the sliding blocks on the sliding bevels.

Optionally, grooves are formed in the bottom of the sliding sleeve; each sliding bevel is connected with each groove; and when the sliding blocks slide into the grooves along the sliding bevels, the sliding blocks are limited in the grooves. Therefore, the sliding blocks can be blocked into the grooves to be fixed after the positions are changed, and the sliding blocks are jammed, so as to avoid recovering under the effect of external force, so that the safety is improved.

Optionally, a cambered surface is formed at the top of each sliding block, and the cambered surfaces push against the sliding bevels. Therefore, the resistance can be reduced when the sliding blocks slide on the sliding bevels.

Optionally, the injection pen needle also comprises an elastic element which is used for driving the limit ring to move upwards; the elastic element is arranged in the outer sleeve; and the upper end and the lower end of the elastic element respectively push against the limit ring and the needle seat to drive the limit ring to move up and down. Therefore, the displacement of the two ends of the elastic element is limited, and the limit ring is driven to move downwards and then move upwards to be recovered.

Optionally, spacing strips extending along an axial direction are arranged on the inner wall of the outer sleeve, a first sliding rail and a second sliding rail are respectively formed in the two sides of each spacing strip, and the sliding blocks are adapted to move in the first sliding rails and the second sliding rails. Therefore, the sliding blocks can be limited to sequentially move in the first sliding rails and the second sliding rails.

Optionally, bumps are also arranged on the side wall of the sliding sleeve, the bottom of each bump is adapted to push against each sliding block, and the bumps are adapted to move along the first sliding rails. Therefore, the contact area that the bottom of the sliding sleeve pushes against the sliding blocks is increased, the lean-against stability is ensured, and meanwhile, the sliding blocks are conveniently pushed into the sliding bevels to further slide.

Optionally, a neck is formed in each baffle plate, blocking strips are arranged on the inner wall of the outer sleeve, and the blocking strips enter the necks to form blocking connection. Therefore, the connection stability of the outer sleeve and a cutter seat is improved.

Optionally, at least one sliding block is distributed uniformly along a circumferential direction of the side wall of the limit ring. Therefore, the number of sliding blocks is set according to actual demands; and by arranging a plurality of sliding blocks, force bearing points of the limit ring can be increased, so as to enhance the pressure bearing capacity of the limit ring and improve the safety.

Optionally, the injection pen needle also comprises a protective sleeve, and the protective sleeve is adapted to be arranged on the outer sleeve in a covering manner. Therefore, the protective sleeve has the effect of protection, so as to avoid that the needle head is exposed due to false touch when in use to cause an injury, and further improve the overall safety; and meanwhile, the protective sleeve has the effect of protecting the interior, so as to avoid the damage caused by collision.

DESCRIPTION FOR REFERENCE NUMERALS IN THE DRAWINGS

Figure 1:
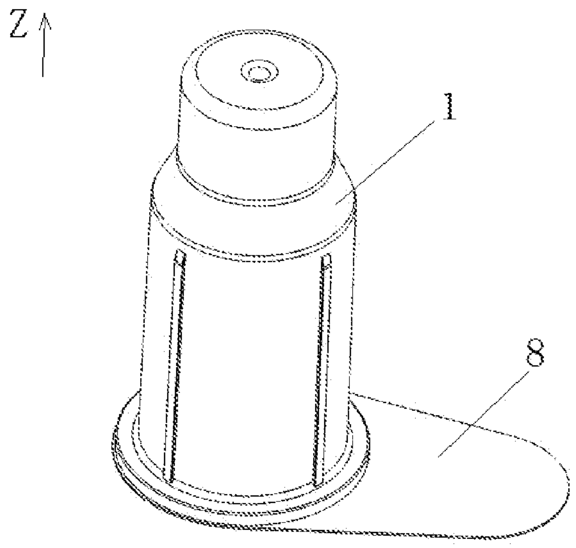
FIG. 1 is an overall structural diagram of an injection pen needle in an embodiment of the utility model.

1—protective sleeve, 2—needle head, 3—needle seat, 31—baffle plate, 311—neck, 4—outer sleeve, 41—spacing strip, 42—first sliding rail, 43—second sliding rail, 44—blocking strip, 45—flange, 5—sliding sleeve, 51—sliding bevel, 52—groove, 53—bump, 6—limit ring, 61—sliding block, 611—cambered surface, 7—elastic element, and 8—sealing strip.

DETAILED DESCRIPTION OF THE UTILITY MODEL

To make purposes, technical solutions and advantages of the embodiments of the present disclosure clearer, the technical solutions in the embodiments of the present disclosure will be clearly and fully described below in combination with the drawings in the embodiments of the utility model. Apparently, the described embodiments are merely part of the embodiments of the utility model, not all of the embodiments. The components of embodiments of the utility model, which are generally described and shown in the drawings herein, can be arranged and designed in a variety of different configurations.

Therefore, the following detailed description of the embodiments of the present disclosure provided in the drawings is not intended to limit the scope of the claimed utility model, but merely to indicate selected embodiments of the utility model. Based on the embodiments in the utility model, all other embodiments obtained by those ordinary skilled in the art without contributing creative labor will belong to the protection scope of the utility model.

It should be noted that similar reference numerals and letters indicate similar items in the following drawings. Therefore, once an item is defined in one drawing, the item does not need to be further defined and explained in subsequent drawings.

It should be indicated in the description of the present disclosure that terms such as “upper”, “lower”, “left”, “right”, “inner”, “outer”, “front”, “rear”, etc. indicate direction or position relationships shown based on the drawings, or conventionally placed direction or position relationships of the product of the present disclosure when used, and are only intended to facilitate the description of the present disclosure and the simplification of the description rather than to indicate or imply that the indicated device or element must have a specific direction or constructed and operated in a specific direction, and therefore, shall not be understood as a limitation to the utility model. In the drawings of the embodiments of the utility model, a coordinate system Z-axis is provided, the positive direction of the Z-axis represents the upper side, and the reverse direction of the Z-axis represents the lower side.

It should also be indicated in the explanation of the present disclosure that, unless otherwise specifically regulated and defined, terms such as “installation”, “arrangement”, “connected”, etc. shall be understood in broad sense. For example, “connection” may refer to fixed connection or detachable connection or integral connection, may refer to mechanical connection or electrical connection, and may refer to direct connection or indirect connection through an intermediate medium or inner communication of two elements. For those ordinary skilled in the art, the specific meanings of the above terms in the present disclosure may be understood according to specific conditions.

The preferred embodiments of the present disclosure are described below in combination with the drawings. It should be understood that the preferred embodiments described herein are only used to illustrate and explain the present disclosure and are not intended to limit the utility model.

Combining with FIG. 1-FIG. 5, an embodiment of the present disclosure provides an injection pen needle, which comprises: a needle head 2, a needle seat 3, an outer sleeve 4, a sliding sleeve 5 and a limit ring 6; the needle head 2 is arranged on the needle seat 3; the needle head 2 axially penetrates through the center of the needle seat 3; baffle plates 31 are arranged on the needle seat 3; the needle seat 3 enters into the outer sleeve 4 from the bottom of the outer sleeve 4; the needle seat 3 is arranged in the outer sleeve 4 in a sleeving manner; the lower part of the sliding sleeve 5 enters the outer sleeve 4 and can move up and down in the outer sleeve 4; a channel hole, from which the needle head 2 can penetrate out, is formed in the top of the sliding sleeve 5; when not in use, the needle head 2 does not penetrate out from the top of the sliding sleeve 5, and the needle head 2 is completely shielded by the sliding sleeve 5; when in use, pressure is exerted on the sliding sleeve 5 to enable the sliding sleeve 5 to move downwards, so that the needle head 2 penetrates out from the channel hole in the top of the sliding sleeve 5; the limit ring 6 is arranged in the outer sleeve 4; the limit ring 6 comprises sliding blocks 61; the bottom of the sliding sleeve 5 pushes against the limit ring 6; when the sliding sleeve 5 moves up and down in the outer sleeve 4, the limit ring 6 is rotated relatively to the sliding sleeve 5, and the sliding blocks 61 are moved to the positions which are above the baffle plates 31; when the sliding sleeve 5 moves downwards for a second time, the sliding blocks 61 lean against the baffle plates 31 to limit the sliding sleeve 5 to move downwards further; the baffle plates 31 have the effect of limiting a moving stroke of the limit ring 6, so as to effectively prevent the needle head 2 from stretching out from the channel hole in the top of the sliding sleeve 5 again to cause puncturing, and further improve the safety.

Combining with FIG. 3-FIG. 5 and FIG. 10, sliding bevels 51 are formed at the bottom of the sliding sleeve 5; each sliding bevel 51 pushes against each sliding block 61; the sliding sleeve 5 and the limit ring 6 move jointly; and when the sliding sleeve 5 is pressed to move downwards, the sliding sleeve 5 pushes the limit ring 6 to move downwards synchronously, and meanwhile, the sliding blocks 61 on the limit ring 6 are moved on the sliding bevels 51, so that the limit ring 6 is rotated, so as to change the positions of the sliding blocks 61 after movement.

In other implementation manners, the sliding bevels 51 can be replaced by cambered surfaces, or surfaces with a guiding function, which are formed through joining of cambered surfaces and bevels, and so on.

Figure 3:
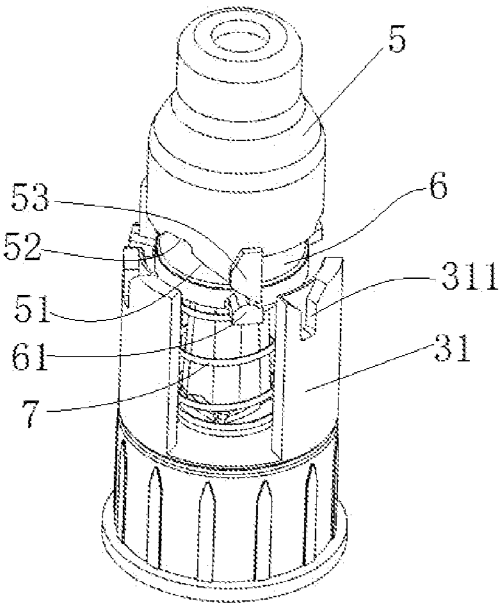
FIG. 3 is a state diagram before a limit ring and the sliding sleeve are used in the embodiment of the utility model.
Figure 10:
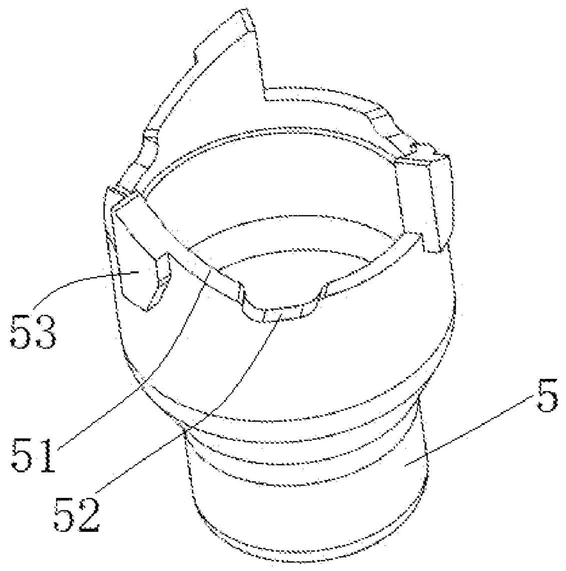
FIG. 10 is a structural diagram of the sliding sleeve in the embodiment of the utility model.

Combining with FIG. 3 and FIG. 10, grooves 52 are formed in the bottom of the sliding sleeve 5; each sliding bevel 51 is connected with each groove 52; the sliding blocks 61 move along the sliding bevels 51 and finally enter the grooves 52; the grooves 52 are large enough to enable the whole sliding blocks 61 to be embedded into the grooves 52 or enable parts of the sliding blocks 61 to be embedded into the grooves 52; and through the arrangement of the grooves 52, the sliding blocks 61 can be fixed at designated positions after moving along with the bevels, so as to prevent the positions of the sliding blocks 61 from being changed under the effect of external force to affect the using effect.

Figure 4:
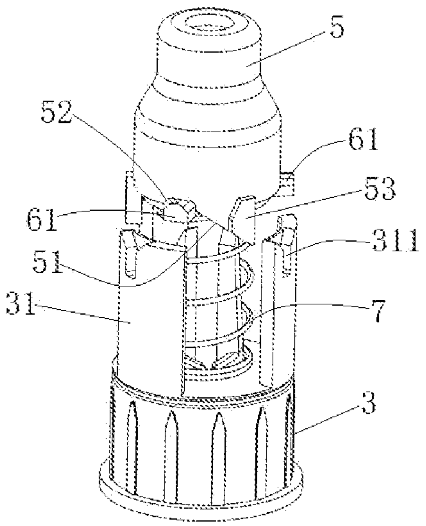
FIG. 4 is a state diagram after the limit ring and the sliding sleeve are used in the embodiment of the utility model.

Combining with FIG. 4, a cambered surface 611 is formed at the top of each sliding block 61; when the sliding blocks 61 push against the sliding sleeve 5, the cambered surfaces 611 push against the sliding bevels 51; the frictional force can be reduced by the cambered surfaces 611, so that the sliding blocks 61 can slide along the cambered surfaces 611 more smoothly, thereby avoiding generation of a blocking phenomenon when the sliding sleeve 5 is pressed downwards in a using process.

Figure 5:
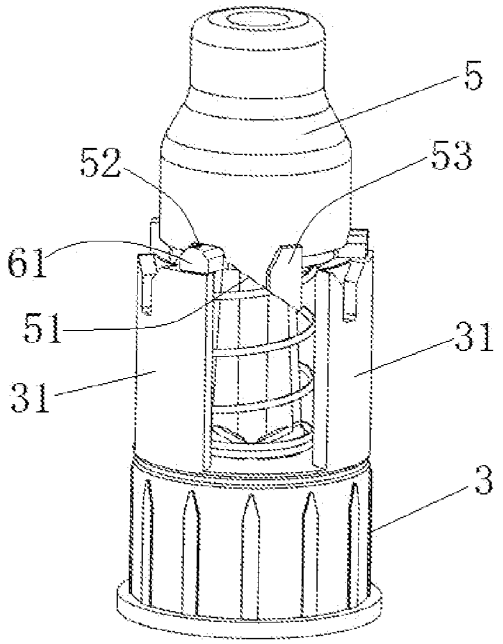
FIG. 5 is a state diagram that sliding blocks push against baffle plates in the embodiment of the utility model.

Combining with FIG. 3-FIG. 5, the injection pen needle also comprises an elastic element 7; the elastic element 7 is used for driving the limit ring 6 to move up and down, so that when the limit ring 6 is pressed to move downwards, the elastic element 7 is compressed, so as to provide elastic potential energy for the limit ring 6; when the pressure is removed, the elastic element 7 can push the limit ring 6 to return to an original height position; the elastic element 7 is arranged in the outer sleeve 4; the elastic element 7 is arranged in a cavity formed by the needle seat 3 and the outer sleeve 4 along an axial direction; and meanwhile, the upper end and the lower end of the elastic element 7 respectively push against the limit ring 6 and the needle seat 3, so as to limit the displacement of the two ends of the elastic element 7. In the embodiment, the elastic element 7 is a spring.

Figure 6:
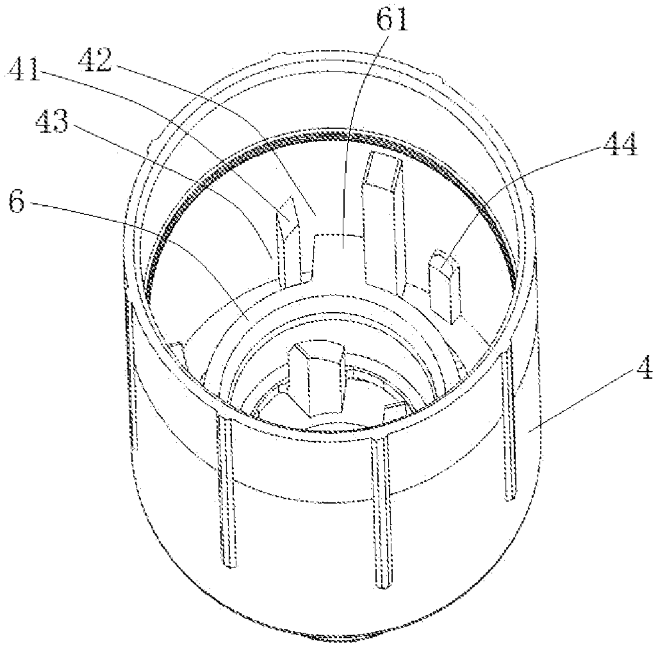
FIG. 6 is an assembly diagram of a locking ring and the outer sleeve in the embodiment of the utility model.

Combining with FIG. 6, spacing strips 41 extending along the axial direction are arranged on the inner wall of the outer sleeve 4; a first sliding rail 42 and a second sliding rail 43 that extend along the axial direction of the outer sleeve 4 and are sunken towards the inner wall of the outer sleeve 4 are respectively formed in the two sides of each spacing strip 41; and the sliding blocks 61 are adapted to move in the first sliding rails 42 and the second sliding rails 43. When the sliding sleeve 5 is pressed, the sliding sleeve 5 and the limit ring 6 move downwards synchronously, the sliding blocks 61 move downwards in the first sliding rails 42, and the limit ring 6 is rotated through movement of the sliding blocks 61 on the sliding bevels 51; when the sliding blocks 61 move out from the bottoms of the first sliding rails 42, the sliding blocks 61 are rotated across the bottoms of the spacing strips 41 and enter the second sliding rails 43 from the bottoms of the second sliding rails 43; when the limit ring 6 moves upwards, the sliding blocks 61 move upwards in the second sliding rails 43 and are finally rotated to the positions which are above the baffle plates 31, so as to limit the sliding sleeve 5 to move downwards for a second time; and the sliding blocks 61 are limited by the spacing strips 41 to sequentially move only in the first sliding rails 42 and the second sliding rails 43.

Combining with FIG. 3-FIG. 5 and FIG. 10, bumps 53 are also arranged on the side wall of the sliding sleeve 5; the bottom of each bump 53 pushes against each sliding block 61; the bumps 53 can just enter the first sliding rails 42 and can move in the first sliding rails 42, so that the contact area that the bottom of the sliding sleeve 5 pushes against the sliding blocks 61 is increased; the stability that the bottom of the sliding sleeve 5 pushes against the sliding blocks 61 is further improved; and meanwhile, the sliding blocks 61 are conveniently pushed into the sliding bevels 51 to further slide, and the sliding sleeve 5 is limited into the outer sleeve 4 by the bumps 53.

Figure 2:
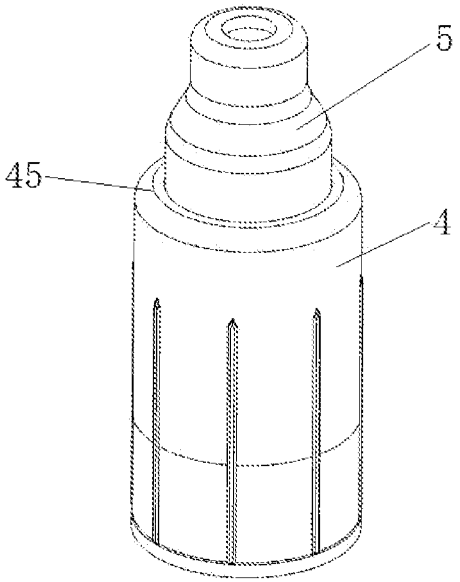
FIG. 2 is an assembly diagram of a sliding sleeve and an outer sleeve in the embodiment of the utility model.
Figure 8:
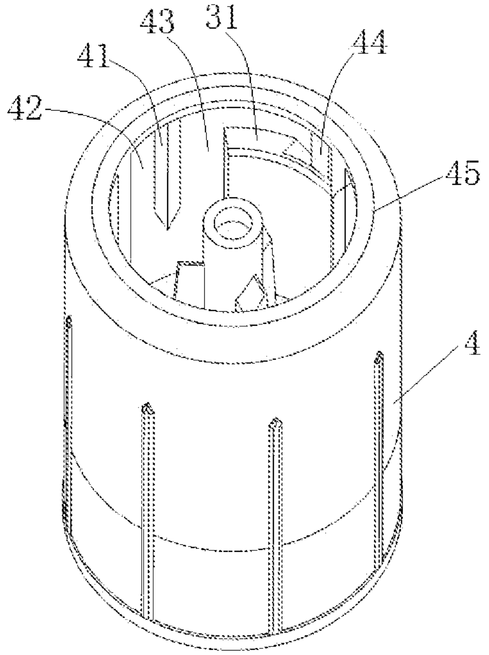
FIG. 8 is an assembly diagram of the needle seat and the outer sleeve in the embodiment of the utility model.

Combining with FIG. 2 and FIG. 8, in the embodiment, a ring-shaped flange 45 is also arranged on the inner wall of the outer sleeve 4; and when the outer sleeve 4 is arranged on the needle seat 3 in a sleeving manner, the flange 45 pushes against the tops of the bumps 53, so that the sliding sleeve 5 is limited into the outer sleeve 4, thereby ensuring that the sliding sleeve 5 can move only in the outer sleeve 4 in a moving process.

Figure 7:
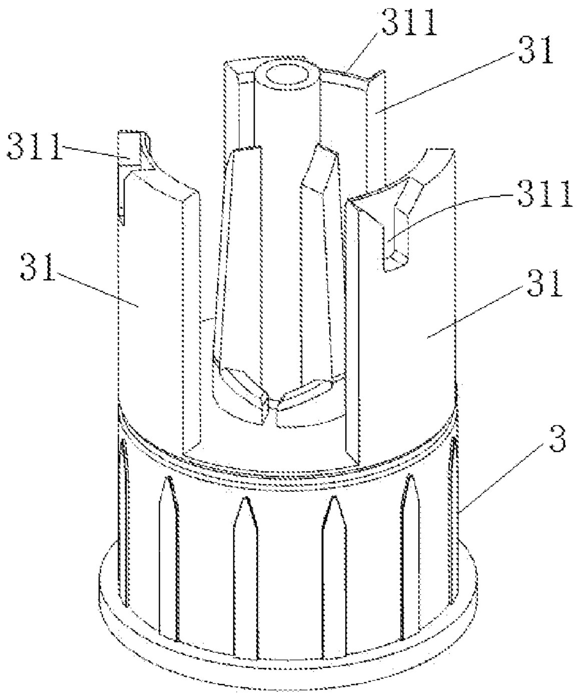
FIG. 7 is a structural diagram of a needle seat in the embodiment of the utility model.

Combining with FIG. 6-FIG. 8, a neck 311 is formed in the side wall of each baffle plate 31; a blocking strip 44 adaptive to each neck 311 is arranged on the inner wall of the outer sleeve 4; and when the outer sleeve 4 is arranged on the needle seat 3 in a sleeving manner, the blocking strips 44 are inserted into the necks 311, so that the outer sleeve 4 is fixedly connected with the needle seat 3, thereby avoiding that the outer sleeve 4 falls off from the needle seat 3 and improving the using safety.

Further, in the embodiment, the number of baffle plates 31 is three; the three baffle plates 31 are distributed uniformly along a circumferential direction of the needle seat 3; each neck 311 is formed in each baffle plate 31; and through increase of the number of the baffle plates 31, the connection stability of the needle seat 3 and the outer sleeve 4 can be further improved. In other implementation manners, the number of the baffle plates 31 may be one or more.

The number of sliding blocks 61 is at least one; all sliding blocks 61 are respectively and uniformly distributed along a circumferential direction of the limit ring 6; and through increase of the number of the sliding blocks 61, force bearing points of the limit ring 6 can be increased, so as to enhance the pressure bearing capacity of the limit ring 6, avoid the breakage of the sliding blocks 61 caused by excessive pressure to lose the protective effect, and further improve the safety. In the embodiment, the number of the sliding blocks 61 is three, and the three sliding blocks 61 respectively correspond to the three baffle plates 31 in the embodiment. In other implementation manners, the number of the sliding blocks 61 may be one or more.

Combining with FIG. 1, the injection needle head 2 also comprises a protective sleeve 1; the protective sleeve 1 is arranged on the outer sleeve 4 in a sleeving manner; and the protective sleeve 1 can be used for preventing the needle head 2 from being exposed to puncture hands as the sliding sleeve 5 is touched carelessly when the needle head is picked up in use, thereby ensuring the using safety.

Further, a sealing strip 8 is arranged at the bottom of the protective sleeve 1, so as to ensure the leakproofness in the protective sleeve 1 and avoid the contact between the needle head 2 in the needle seat 3 and air to breed bacteria; and the protective sleeve 1 always keeps a germ-free condition when the sealing strip 8 is not torn, so as to ensure the using health.

Figure 9:
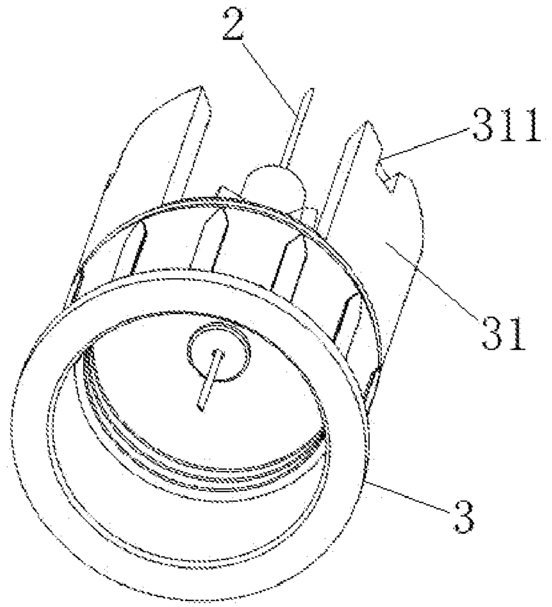
FIG. 9 is an assembly diagram of the needle seat and a needle head in the embodiment of the utility model.

Combining with FIG. 9, the needle head 2 penetrates through two ends of the needle seat 3; screw threads are arranged at the bottom of the needle seat 3 and are used for connecting an injector; and when the injector is connected with the bottom of the needle seat 3, drugs in the injector can be directly transported into a body of a patient through the needle head 2.

In the illustration of this description, the illustration of reference terms "embodiments", "one embodiment", "one implementation", etc. means that specific features, structures, materials or characteristics illustrated in combination with the embodiment or implementation are included in at least one embodiment or implementation of the utility model. In this description, exemplary statements for the above terms do not must aim at the same embodiment or implementation. Moreover, the described specific features, structures, materials or characteristics can be combined appropriately in any one or more embodiments or implementations.

Finally, it should be noted that the above embodiments are only used for describing the technical solution of the utility model, rather than the limit to technical solution of the utility model. Although the present disclosure is described in detail with reference to the above embodiments, those skilled in the art shall understand that the technical solution recorded in each of the above embodiments can be still amended, or some or all of technical features therein can be replaced equivalently. The modifications or replacements shall not make the essence of the corresponding technical solution depart from the scope of the technical solutions of the embodiments of the utility model.

The invention claimed is:

1. An injection pen needle, comprising:

a needle head (2);

a needle seat (3), wherein the needle head (2) is arranged on the needle seat (3), and the needle seat (3) comprises baffle plates (31);

an outer sleeve (4), wherein the outer sleeve (4) is arranged on the needle seat (3) in a sleeving manner;

a sliding sleeve (5), wherein a lower part of the sliding sleeve (5) enters the outer sleeve (4) and is adapted to move up and down in the outer sleeve (4), and a channel hole, from which the needle head (2) can penetrate out, is formed in a top of the sliding sleeve (5); and a limit ring (6), wherein the limit ring (6) is arranged in the outer sleeve (4); the limit ring (6) comprises sliding blocks (61); a bottom of the sliding sleeve (5) pushes against the limit ring (6); and when the sliding sleeve (5) moves up and down in the outer sleeve (4), the limit ring (6) is adapted to rotate relatively to the sliding sleeve (5) to enable the sliding blocks (61) to move to the positions which are above the baffle plates (31), wherein sliding bevels (51) are formed at the bottom of the sliding sleeve (5), each sliding bevel (51) of the sliding bevels (51) pushes against each sliding block (61) of the sliding blocks (61), and the sliding blocks (61) are adapted to move along the sliding bevels (51).

2. The injection pen needle according to claim 1, wherein grooves (52) are formed in the bottom of the sliding sleeve (5); each sliding bevel (51) is connected with each groove (52) of the grooves (52); and when the sliding blocks (61) slide into the grooves (52) along the sliding bevels (51), the sliding blocks (61) are limited into the grooves (52).

3. The injection pen needle according to claim 1, wherein a cambered surface (611) is formed at a top of each sliding block (61), and the cambered surfaces (611) push against the sliding bevels (51).

4. The injection pen needle according to claim 1, further comprising an elastic element (7); the elastic element (7) is arranged in the outer sleeve (4); and a upper end and a lower end of the elastic element (7) respectively push against the limit ring (6) and the needle seat (3) to drive the limit ring (6) to move up and down.

5. The injection pen needle according to claim 1, wherein spacing strips (41) extending along an axial direction are arranged on a inner wall of the outer sleeve (4), the outer sleeve (4) further comprises first sliding rails (42) and second sliding rails (43), each first sliding rail (42) of the first sliding rails and each second sliding rail (43) of the second sliding rails (43) are respectively formed in two sides of each spacing strip (41) of the spacing strips (41), and the sliding blocks (61) are adapted to move in the first sliding rails (42) and the second sliding rails (43).

6. The injection pen needle according to claim 5, wherein bumps (53) are also arranged on a side wall of the sliding sleeve (5), a bottom of each bump (53) of the bumps is adapted to push against each sliding block (61) of the sliding blocks, and the bumps (53) are adapted to move along the first sliding rails (42).

7. The injection pen needle according to claim 1, wherein a neck (311) is formed in each baffle plate (31) of the baffle plates, blocking strips (44) are arranged on an inner wall of the outer sleeve (4), and each blocking strip of the blocking strips (44) enter the neck (311) of each baffle plate (31) of the baffle plates to form blocking connection.

8. The injection pen needle according to claim 1, wherein at least one sliding block (61) of the sliding blocks is distributed uniformly along a circumferential direction of a side wall of the limit ring (6).

9. The injection pen needle according to claim 1, further comprising a protective sleeve (1); and the protective sleeve (1) is adapted to be arranged on the outer sleeve (4) in a covering manner.

* * * * *